United States Patent [19]
Hall

[11] Patent Number: 5,614,157
[45] Date of Patent: *Mar. 25, 1997

[54] UNITIZED INFECTIOUS WASTE PROCESSOR AND WASTE PROCESSING METHOD

[75] Inventor: John L. Hall, Tracy, Calif.

[73] Assignees: Darlene Hall; Wilburn E. Hall; Vern W. Hall

[*] Notice: The term of this patent shall not extend beyond the expiration date of Pat. No. 5,389,1347.

[21] Appl. No.: 361,585

[22] Filed: Dec. 22, 1994

Related U.S. Application Data

[63] Continuation-in-part of Ser. No. 130,189, Oct. 1, 1993, Pat. No. 5,389,347.

[51] Int. Cl.[6] .......................................................... A61L 2/04
[52] U.S. Cl. .......................... 422/307; 241/606; 422/308; 422/309
[58] Field of Search .............................. 422/26, 307, 308, 422/309, 269, 273, 285, 286, 282; 241/606; 110/223

[56] References Cited

U.S. PATENT DOCUMENTS

| | | | |
|---|---|---|---|
| 2,731,208 | 1/1956 | Dodd. | |
| 3,589,276 | 6/1971 | Swallert | 100/90 |
| 4,201,128 | 5/1980 | Whitehead | 100/45 |
| 4,374,491 | 2/1983 | Stortroen | 100/73 |
| 4,618,103 | 10/1986 | Wilson et al. | 241/41 |
| 4,809,915 | 3/1989 | Koffsky et al. | 241/36 |
| 5,084,250 | 1/1992 | Hall | 422/292 |
| 5,089,228 | 2/1992 | Meijer | 422/37 |
| 5,223,231 | 6/1993 | Drake | 422/297 |
| 5,294,412 | 3/1994 | Orlando | 422/295 |
| 5,340,536 | 8/1994 | Datar et al. | 422/309 X |
| 5,389,347 | 2/1995 | Hall | 422/307 |

Primary Examiner—Robert J. Warden
Assistant Examiner—Krisanne M. Thornton
Attorney, Agent, or Firm—Harris Zimmerman

[57] ABSTRACT

Apparatus for treating infectious wastes from hospitals, medical clinics or the like integrates sterilizing, fragmentizing and compaction steps within a single waste processor. Wastes which are deposited in a sterilization chamber are made non-infectious by exposure to pressurized steam. An outflow of wastes from the sterilization chamber is fed through one or more on-line shredders or the like and then into a compactor which compresses the processed material into a transportable container that may be hauled to a dump site.

19 Claims, 6 Drawing Sheets

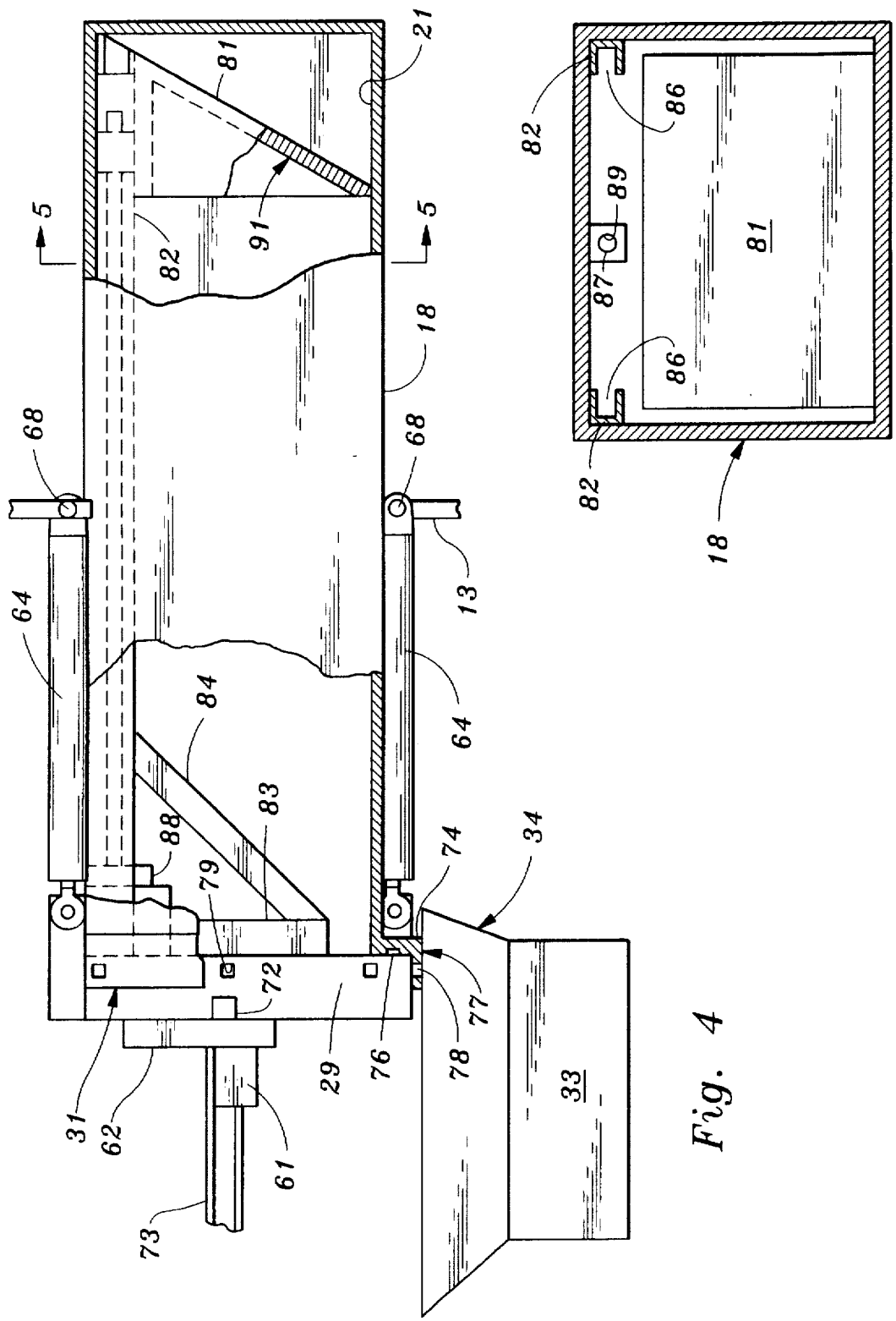

UNITIZED INFECTIOUS WASTE PROCESSOR AND WASTE PROCESSING METHOD

CROSS REFERENCE TO RELATED APPLICATION

This is a continuation-in-part of application Ser. No. 08/130,089 (now U.S. Pat. No. 5,389,347) filed Oct. 1, 1993 and which is entitled "Bio-Hazardous Waste Sterilizer and Compactor".

TECHNICAL FIELD

This invention relates to the processing of waste materials which may be infectious and more particularly to apparatus and a method for storing, sterilizing and compacting such wastes prior to delivery of the wastes to a dump site or the like.

BACKGROUND OF THE INVENTION

Waste materials that are generated at hospitals, medical clinics or the like may be infectious and require specialized processing prior to disposal of the wastes at a dump site. The accumulating wastes should be stored in a sealed receptacle. Periodically, the accumulated wastes are sterilized such as by exposure to high pressure steam to assure that all infectious organisms are destroyed. The wastes are then transferred to a transportable container for delivery to the dump site. Hauling costs can be reduced by compacting the sterilized waste as it is being transferred to the container. Prior U.S. Pat. Nos. 4,374,491 and 5,084,250 describe a type of waste processor which is capable of performing each of these operations.

Infectious wastes from hospitals or the like may include diverse different objects and materials such as used bandages and tissues, hypodermic needles, specimen containers and hard metal prostheses among other examples. It is preferable that the mixture of diverse different objects be shredded, ground up, pulverized or be otherwise reduced to small fragments. This enables greater compaction of the material and breaks up sharp objects in the waste that can otherwise be potentially hazardous. Shredding or the like also makes it apparent to handlers that the waste has been processed and is now harmless. The fragmented material is also unrecognizable as medical waste by casual observers and thereby avoids needless apprehension by persons who may encounter the wastes.

As heretofore practiced, the fragmentizing operation has complicated the handling of the wastes and added substantially to the costs of processing the wastes. Unloading the sterilized wastes from the sterilizing chamber and reloading the wastes into a shredder or the like and then transferring the material from the shredder or the like to a container requires a significant amount of time and effort.

The last mentioned portion of this effort is avoided by apparatus described in prior U.S. Pat. No. 5,294,412. This prior patent discloses a truck vehicle for transporting sterilized wastes to the dump site which carries a shredder and a compactor on the bed of the truck itself. Waste is unloaded from the sterilizer and deposited in receptacles which, when the specialized truck arrives, are lifted and dumped into the shredder which is carried on the truck. Thus the process continues to require multiple loadings and unloadings of the waste material during the course of the process.

Prior devices for fragmentizing wastes in this particular context require a compromise between efficient high speed operation and the degree of fragmenting that is realized. For example, shredders with large cutting blades that are most suitable for shredding large metal objects produce correspondingly large fragments. Shredders which produce desirably fine fragments do not shred such objects in a desirably efficient manner.

The present invention is directed to overcoming one or more of the problems discussed above.

SUMMARY OF THE INVENTION

In one aspect, the present invention provides a bio-hazardous waste material processing installation having a sterilizer which includes a sterilizing chamber for receiving the waste material and waste material ejection means for discharging a flow of sterilized waste material from the chamber. A compactor has a sterilized waste material receiving compartment and means for forcing the contents of the compartment into an adjacent receptacle which is separable from the compactor and which may be transported to a dump site or the like. The apparatus further includes at least one waste material fragmentizer having an intake positioned to receive the flow of sterilized waste material as it is being discharged from the sterilizing chamber and having means for concurrently delivering a flow of fragmentized sterilized waste material to the compactor compartment.

In another aspect of the invention, the fragmentizer has first fragmenting means for reducing the waste material to pieces of a first maximum size and has second fragmenting means for reducing the pieces of a first maximum size to pieces of a smaller maximum size.

In another aspect of the invention, apparatus for processing bio-hazardous waste material includes an upwardly extending support framework having a lower region, an intermediate region and an upper region. A waste compactor is situated at the lower region of the framework and is secured thereto, the compactor having a horizontally extending waste material compartment with an open end and means for forcing the contents of the compartment out of the open end. A waste material sterilizer is disposed at the upper region of the framework and has a sealable sterilizing chamber for receiving the bio-hazardous waste material and means for injecting pressurized steam into the chamber to sterilize the contents thereof. The chamber has a sterilized waste material discharge opening at one end which chamber end is horizontally spaced apart from the location of the open end of the compactor compartment. Further components include means for discharging sterilized waste material from the chamber through the discharge opening and a waste material fragmentizer situated at the intermediate region of the framework. The fragmentizer is horizontally spaced apart from the location of the open end of the compactor compartment by a distance that is smaller than the spacing of the end of the sterilization chamber therefrom. The fragmentizer has an intake located to receive waste material that is discharged from the sterilization chamber and has an outlet from which fragmented waste material is delivered to the compactor compartment.

In still another aspect, the invention provides a method of processing bio-hazardous waste materials which includes the step of subjecting the waste materials to pressurized steam within a sealed chamber for a period sufficient to sterilize said waste materials. The waste material is then fragmented by directing an outflow of waste material from the chamber into a fragmentizer. Concurrently, an outflow of the fragmented sterilized waste material from the fragmentizer is directed into a compactor. The sterilized and fragmented waste material is then compacted into a transportable container for delivery to a dump site.

The invention provides a single unitized waste processor which integrates the operations of storing infectious waste material, sterilizing the material, fragmentizing the material and compacting the material into a transportable container. Unloading and reloading of the material between successive stages of the process is unnecessary. This simplifies and speeds handling of the material and thereby effects cost savings. In one form of the invention the fragmentizing operation is accomplished in stages during which the material is reduced to fragments of successively smaller maximum size thereby enabling fast and efficient fragmenting of large hard objects in the material while also providing an end product which contains only very small fragments.

The invention, together with further aspects and advantages thereof, may be further understood by reference to the following description of the preferred embodiments and by reference to the accompanying drawings.

BRIEF DESCRIPTION OF THE DRAWINGS

FIG. 4 is a broken out elevation view of certain internal components of the first embodiment of the invention including a waste sterilizer and a waste fragmentizer.

FIG. 5 is a cross section view of the waste sterilizer of FIG. 4 taken along line 5—5 thereof.

DETAILED DESCRIPTION OF THE PREFERRED EMBODIMENTS

Figure 1:
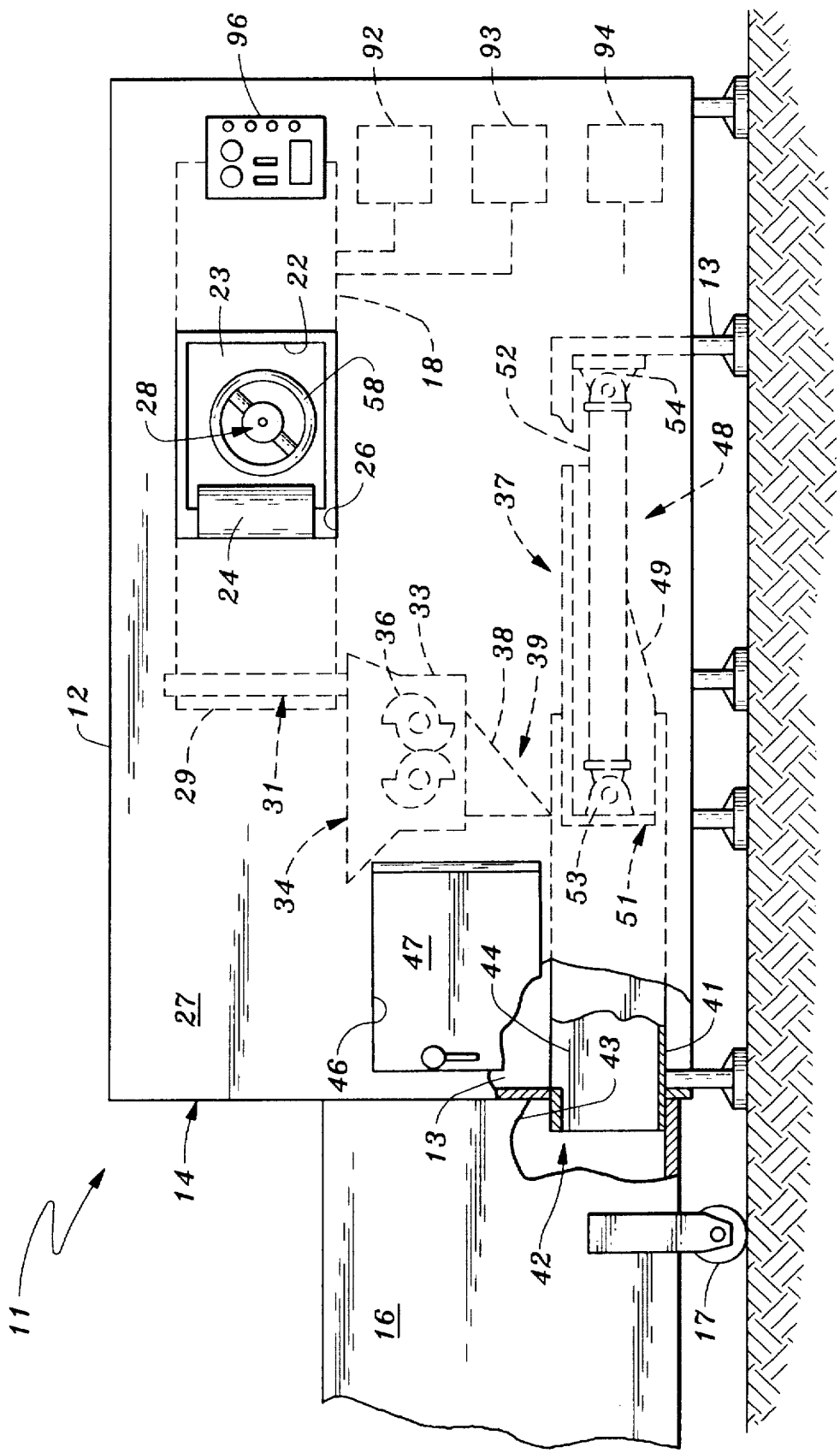
FIG. 1 is a frontal elevation view of an infectious waste processor in accordance with a first embodiment of the invention, portions of the structure being broken out to expose internal components.

Referring initially to FIG. 1 of the drawings, an infectious waste processor 11 in accordance with this embodiment of the invention has a housing 12 supported by framework members 13 and which is of elongated rectangular shape in this example although other configurations are possible. During operation, a first end 14 of housing 12 is abutted by a transportable roll away container 16 into which sterilized and fragmented waste material is compacted as will be further described. When filled, the container 16 is loaded onto a truck and hauled to a landfill or dump site for disposal of the processed wastes. The container 16 of this example has ground wheels 17 which enable the container to be rolled off of a loading dock (not shown) and onto the bed of the truck.

Figure 2:
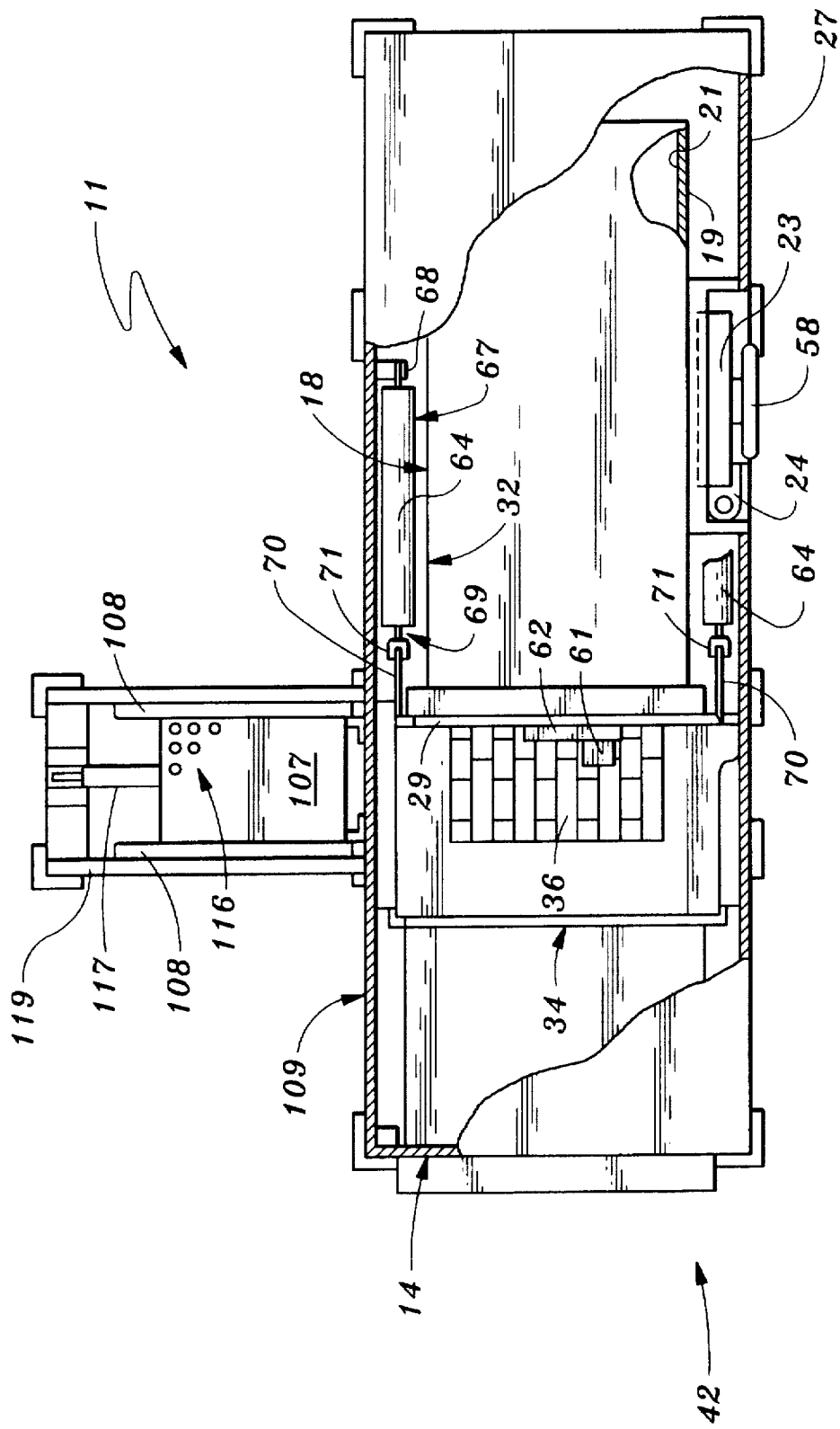
FIG. 2 is a broken out top view of the waste processor of FIG. 1.
Figure 3:
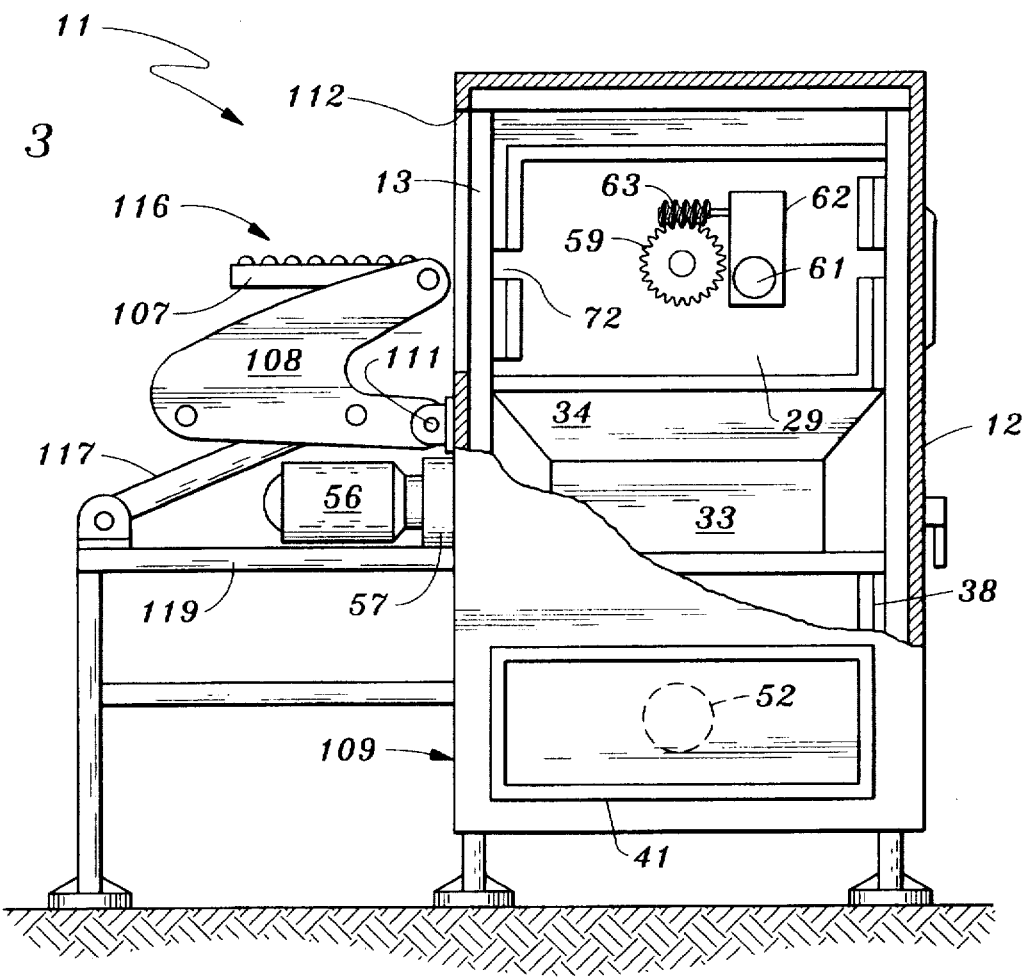
FIG. 3 is a broken out end view of the waste processor of the preceding figures.

Referring jointly to FIGS. 1, 2 and 3, a waste sterilizer 18 is situated within housing 12 at an upper region of the housing and at a location which is away from the first end 14 of the housing. The sterilizer 18 has a rectangular wall 19 bounding a sterilizing chamber 21 into which the wastes which are to be sterilized are deposited. Wastes are entered into chamber 21 through a waste material entry opening 22 at the front of the sterilizer wall 19. Opening 22 can be closed and sealed by a door 23 which is coupled to the sterilizer by a hinge 24 and which is accessible at a recess 26 in the front wall 27 of housing 12. Door 23 is of one of the known types which create a pressure tight seal when closed and latched, the door of this example being of the general type that is used to seal passageways in the bulkheads of ships. Door 23 may be equipped with a key lock 28 to assure that unauthorized persons do not have access to the contaminated contents of the sterilizer 18.

Sterilized wastes are discharged from sterilizer 18 through a second pressure sealing door 29 which may be of the same general type as door 23 and which is situated at a first end 31 of the sterilizer that faces first end 14 of housing 12. Waste ejection means 32 which will hereinafter be described discharges the wastes from sterilizer 18 in the form of a continuous gradual outflow of such wastes.

A waste material fragmentizer, which is a shredder 33 in this example of the invention, is situated at an intermediate level within housing 12 below the waste material discharge door 29 and has an intake hopper 34 positioned to receive the outflow of wastes from sterilizer 18. The shredder 33 may be of any of various known forms and in this example is of the type which has two sets of interleaved counterrotating rotary cutting blades 36. The outflow of shredded wastes from shredder 33 is delivered to a waste compactor 37 by a chute 38 which is situated below the shredder and which has an inclined floor 39 that extends downward and in the direction of first end 14 of housing 12.

Other types of fragmentizer, such as a grinder a chopper or a pulverizer for example, may be substituted for the shredder 33 of this example.

The waste material compactor 37 is situated within a lower region of housing 12 and includes a duct 41 which extends from a location below chute 38 through end 14 of housing 12 and outward from the housing. Duct 41 is of rectangular cross section in this example of the invention and has an open end 42 which extends outward from housing 12 and into a conforming opening 43 is the adjacent end of the roll away waste container 16. The portion of duct 41 that extends from chute 38 to first end 14 of housing 12 is open at the top and forms a compartment 44 for receiving the outflow of sterilized and shredded waste from shredder 33.

The above described arrangement of components locates shredder 33 and chute 38 away from the first end 14 of housing 12 and situates sterilizer 18 a greater distance away from the first end. Thus the space immediately above compactor compartment 44 is unobstructed. This enables direct entry of waste materials that do not require sterilization and/or shredding into the compartment 44. For this purpose, the housing front wall 27 has an opening 46 above the compartment 44 which provides for direct access to the compartment and which is preferably closable by another door 47.

Compactor 37 further includes means 48 for compacting the contents of compartment 44 into the roll away container 16. Such means 48 includes a slidable ram 49 which enters into duct 41 and which has a forward end 51 that conforms with the interior of the duct. Ram 49 is translated along the duct 41 by an extensible and contractible hydraulic actuator 52 of the rod and cylinder type. Actuator 52 has a first end coupled to forward end 51 of ram 49 by a first pivot coupling 53 and an opposite end coupled to a housing framework member 13 by another pivot coupling 54. Actuator 52 is proportioned to drive ram end 51 up to the open end 42 of duct 41 upon full extension of the actuator and to retract the ram end to a location which is below chute 38 upon full contraction of the actuator.

As seen in FIGS. 2 and 3 in particular, the motor 56 which drives shredder 33 is attached to the shredder through a speed reducing gearbox 57 and extends outward from housing 12 at the back of the housing. Motor 56 is an electrical motor in this example but may alternately be a hydraulic motor.

Referring again to FIG. 1, the previously described waste material entry door 23 at sterilizer 18 is of a type that is latched and unlatched by manual turning of a ring 58 in this example of the invention. The waste material discharge door 29 is not accessible for manual operation. At door 29, with reference to FIG. 3, the ring is replaced with a gear wheel 59 which may be turned by a reversible hydraulic motor 61 through a torque multiplying gear box 62 and a gear 63 which components are mounted on the door 29. Gear 63 is a worm gear in this embodiment but other types of gear may be used to couple motor 61 to gear wheel 59. Similar motor driven components may be used to latch and unlatch the waste material entry door 23 to enable automatic cycling of the waste processor 11 under microprocessor control.

The waste material discharge door 29 is not hinged to the sterilizer 18 and is opened by retracting the door away from the first end 31 of the sterilizer. Referring to FIGS. 2 and 3, this is accomplished by a pair of extensible and contractible hydraulic actuators 64 which extend along opposite sides of the sterilizer 18, one actuator being adjacent to the top of the sterilizer and the other being adjacent to the bottom of the sterilizer. The actuators 64 have head ends 67 coupled to the housing framework by pivot couplings 68 and rod ends 69 coupled to opposite corners of door 29 by additional pivot couplings 71 which are secured to sideward extending projections 70 at the opposite corners of the door.

Referring to FIGS. 3 and 4, the waste discharge door 29 is supported by a pair of door members 72 which extend outward from opposite sides of the door. The door members 72 extend into and ride along channel shaped guide rails 73 which are situated at each side of the path of travel of the door and which are secured to housing framework members 13. Referring to FIG. 4 in particular, the door seats against a flange 74 at the first end 31 of sterilizer 18 and in the process compresses an annular resilient seal 76 which extends around the face of the flange thereby assuring sealing of the sterilization chamber 21 when the door is at its closed position. Flange 74 has an annular lip region 77 which is entered by door 29 at the closed position of the door. The latching members 78 of door 29 enter into apertures 79 in the lip region 77 of the flange 74.

Referring to FIGS. 4 and 5, opening of door 29 by extension of hydraulic actuators 64 initiates a gradual outflow of sterilized waste from the sterilizer 18 into shredder intake hopper 34. This is brought about by a waste ejection member 81 which is situated at the opposite end of the sterilization chamber 21 when the door 29 is at its closed position. Ejection member 81 has a height and width which conform with the height and width of the chamber 21 and is coupled to the door 29 as will be further described. Thus the ejection member is pulled towards the first end 31 of sterilizer 18 as door 29 is pushed outward from end 31 by actuators 64. Such travel of the ejection member 81 pushes waste out of the chamber 21 and into shredder intake hopper 34.

Cost and labor savings are realized if the sterilization chamber 21 is voluminous enough to function as a temporary storage for contaminated wastes as they accumulate at the hospital, clinic or the like. This makes it possible to perform the sterilization cycle only periodically as opposed to continuous operation. For this purpose the sterilizer 18 has an elongated shape. The hydraulic actuators 64 must be equally lengthy if the sterilizer 18 is to be fully emptied solely by the above described joint movement of door 29 and ejection member 81. This makes the waste processor as a whole very lengthy. The present embodiment uses shorter actuators 64 and an additional method of traveling ejection member 81 in order to realize space savings.

In particular, the ejection member 81 is linked to the door 29 through a pair of parallel guide rails 82 of channel shaped cross section which extend along opposite sides of the sterilization chamber 21 at the top of the chamber. One end of the rails 82 is secured to the inside surface of door 29 by brackets 83 and diagonal bracing 84 strengthens the connection and imparts rigidity. Ejection member 81 has projections 86 which extend into the guide rails 82. A threaded rod 87 extends in parallel relationship with the rails 82 at a location midway between the rails. Rod 87 is coupled at one end to a reversible rotary hydraulic motor 88 that is secured to the inside surface of the door 29 and which rotates the rod. The rod extends through a passage 89 in ejection member 81 and engages with threads in the passage. Thus rotation of rod 87 by motor 88 in one direction travels ejection member 81 along rails 82 in the direction of door 29 and opposite rotation of the rod travels the member away from the door.

Ejection member 81 preferably has a hollow configuration in which the surface 91 of the member that faces door 29 slopes downward and in the direction of the door. This strengthens the member 81 and assures rigidity.

Referring to FIG. 1, the waste processor 11 contains means 92 for exhausting air from the sterilization chamber 21 at the start of a sterilizing cycle and which also exhausts condensed steam from the chamber during the cycle. Such means 92 may, for example, be of the steam ejector or aspirator type. The processor 11 further includes a steam supply 93 for directing steam to the chamber and a source 94 of pressurized hydraulic fluid for operating the previously described hydraulic components. The vacuum, steam and fluid systems are shown only in schematic form in the drawing as they may each be of the known designs such as are disclosed, for example, in prior U.S. Pat. No. 5,084,250 which is hereby incorporated by reference. Conventional control components for these systems may be mounted at a control console 96 on the front wall 27 of the waste processor 11.

In operation, infectious waste is deposited in the sterilizer 18 through entry door 23 as it accumulates at the hospital, clinic or the like. Such wastes are usually contained in plastic bags which formerly served as liners for waste baskets within the hospital or the like and the wastes remain in the bags when they are deposited in the sterilizer. A sterilizing cycle is begun, when the sterilizer has been filled, by actuating vacuum means 92 to exhaust air from the sterilizer and by actuating steam supply 93 to replace the air with pressurized steam. Steam is applied to the sterilizer 18 for a period which is sufficient to destroy living organisms that are contained in the wastes.

The application of steam to the sterilizer 18 is then stopped and shredder 33 is turned on. Referring to FIG. 4, discharge of waste into the shredder is begun by operating motor 61 to unlatch the discharge door 29 and then by extending hydraulic actuators 64 to travel the door away from end 31 of the sterilizer 18. This also draws ejection member 81 towards the now open end 31 of the sterilizer 18 thereby causing waste material to be pushed out of the open end.

The rate of contraction of actuators 64 is adjusted to outflow waste at a rate that will not overfill the shredder intake hopper 34. This can, if desired, be done automatically by a microprocessor controlled circuit that responds to signals from an ammeter which monitors current flow to the shredder drive motor as the current flow is a function of the load against which the motor is working.

Referring again to FIG. 1, chute 38 delivers the outflow of fragmentized waste from shredder 33 to compactor compartment 44. Compactor ram 49 is reciprocated, periodically or continuously, to force the contents of compartment 44 into the roll away container 16.

Figure 6:
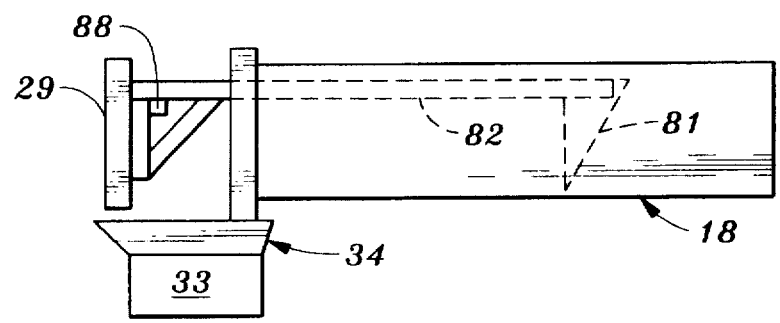
FIG. 6 is diagrammatic elevation view of the waste sterilizer illustrating a stage in the operation thereof.
Figure 7:
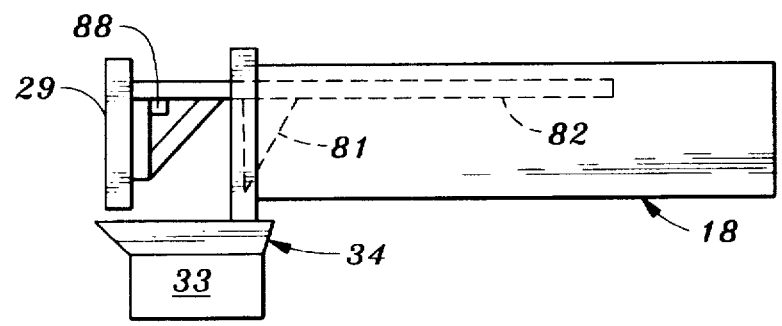
FIG. 7 is another diagrammatic elevation view of the waste sterilizer illustrating a subsequent stage in the operation thereof.

Referring again to FIG. 4, motion of door 29 stops when hydraulic actuators 64 become fully extended. The sterilizer 18 has not been fully emptied at that time as ejection member 81 has not traveled the entire length of the sterilizer and is at an intermediate location as shown in FIG. 6. Travel of the ejection member 81 is then continued by actuating rotary hydraulic motor 88. This travels the ejection member 81 to the open end 31 of the sterilizer 18, as depicted in FIG. 7, in the manner previously described.

After full emptying of the sterilizer 18, hydraulic motor 88 is reversed and actuators 64 are contracted to restore ejection member 81 and door 29 to their original positions. Shredder 33 is shut down and the waste processor is in condition for a subsequent accumulation of wastes and sterilizing cycle.

Manual handling of the wastes during the above described operation of waste processor 11 is confined to the initial deposit of bags of waste in the apparatus. Unloading of partially processed wastes from one piece of equipment and reloading into another is unnecessary.

Referring jointly to FIGS. 2 and 3, fragmentizing of the sterilized wastes by shredder 33 can be expedited by forcing the material against the cutting blades 36 of the shredder. For this purpose, the waste processor 11 may include a feed ram 107 for exerting downward pressure on the bags of sterilized wastes that have been deposited in the intake hopper 34 of the shredder 33. Mechanism for supporting and traveling the feed ram includes arcuate, spaced apart pivotable arms 108 having lower ends coupled to the back wall 109 of the waste processor housing 12 by pivot couplings 111 at a location which is adjacent to the shredder intake hopper 34. Pivot couplings 111 are situated below a window 112 in housing back wall 109 which enables pivoting of the arms 108 between a first location at which the arms are outside of housing 12 and away from the path of travel of discharge door 29 as shown by solid lines in FIG. 8 and a second location at which the distal ends 113 of the arms are within hopper 34 as shown by dashed lines in FIG. 8.

Figure 9:
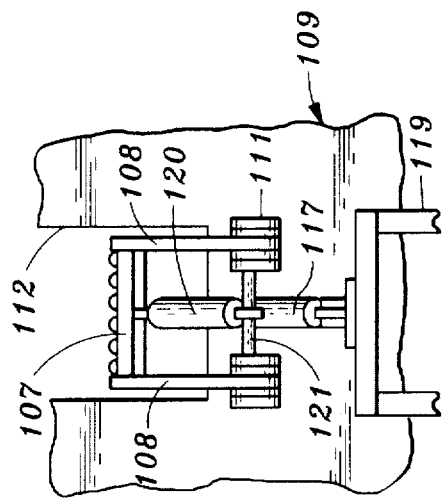
FIG. 9 is a side view of the apparatus of FIG. 8 taken along line 9—9 thereof.
Figure 8:
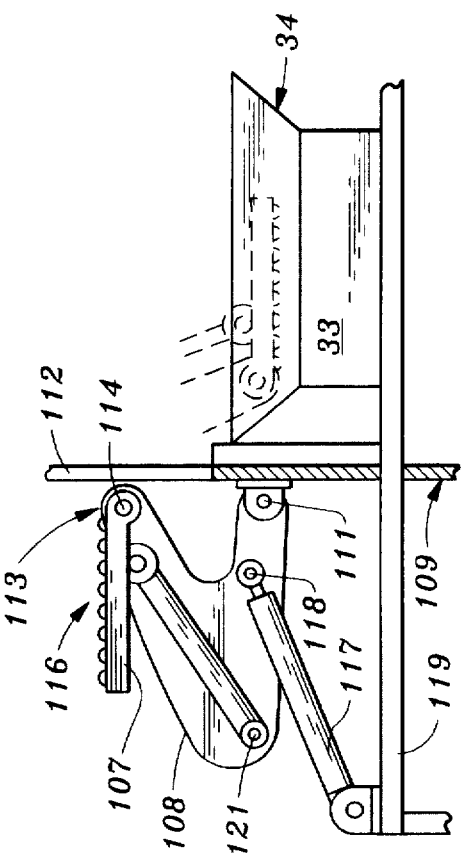
FIG. 8 is a section view of a portion of the apparatus taken along staggered line 8—8 of FIG. 2.

Referring jointly to FIGS. 8 and 9, the feed ram 107 is a plate having an edge which extends between the distal ends 113 of arms 108 and which is pivotably coupled to the arms by an axle shaft 114. Thus the feed ram 107 may be pivoted relative to arms 108 as it is traveled into intake hopper 34 to maintain the ram in a parallel relationship with the base of the hopper and to thereby exert a uniform downwardly directed pressure on the waste materials. The ram is preferably provided with pointed teeth 116 in order to resist sideward displacement of the bags of waste.

Motor means for pivoting the arms 108 and feed ram 107 includes a first extendible and contractible hydraulic actuator 117 having a rod end which is pivoted to a cross shaft 118 that extends between the arms and having a head end pivotably coupled to an extension 119 of the waste processor framework that extends rearward from the housing back wall 109. A second actuator 120 of the same type has a rod end pivoted to the back of the feed ram 107 at a location that is spaced apart from axle shaft 114 and a head end pivoted to another cross shaft 121 that extends between arms 108 at a location that is spaced apart from cross shaft 118.

Referring jointly to FIGS. 3 and 8, feed ram 107 is retracted out of the waste processor housing 12 while discharge door 29 is being opened. Thereafter, arms 108 are pivoted by extension of first actuator 117 to bring the feed ram 107 into housing 12 and the ram is pivoted relative to the arms by extension of second actuator 120 to position it over the waste material in hopper 34. Contined extension of both actuators 117 and 120 then lowers the feed ram while maintaining it is parallel relationship with the base of the hopper. Discharge of wastes from sterilizer 18 into the hopper 34 may be temporarily halted while the feed ram 107 is forcing previously discharged wastes into the shredder 33 in this manner. The feed ram 107 is then retracted by reversing the above described actuators 117 and 120 operations and a new batch of wastes is discharged into the hopper 34 in preparation for a subsequent cycling of the feed ram 107. Operation of the feed ram 107 may be automatically controlled by a microprocessor if desired.

Figure 11:
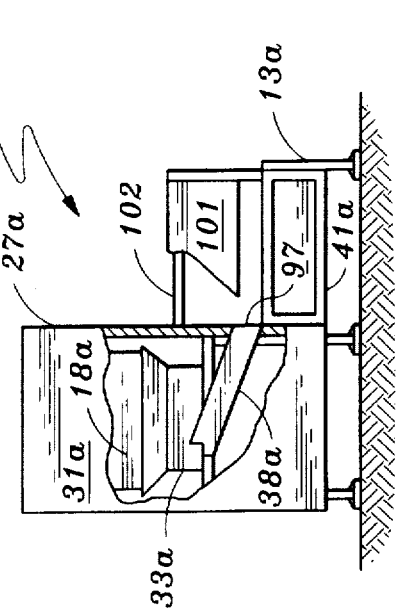
FIG. 11 is a broken out end view of the second embodiment of the invention.
Figure 10:
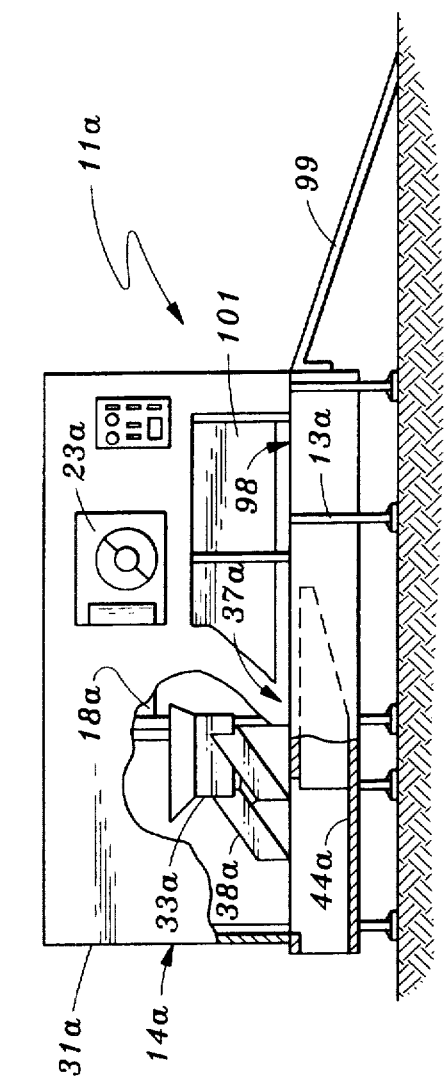
FIG. 10 is broken out front elevation view of another infectious waste processor in accordance with a second embodiment of the invention.

It is desirable that the manual effort that is involved in loading bags of waste into the waste processor be minimized. FIGS. 10 and 11 depict a second embodiment of the invention that facilitates the depositing of bags of waste although the apparatus occupies more surface area than the previously described embodiment.

In the waste processor 11a of FIGS. 10 and 11, the compactor 37a is situated outside of the waste processor housing 12a and extends in parallel relationship with the housing front wall 27a. Additional framework members 13a form legs which support the side of the compactor 37a that is spaced outward from the front wall 27a. The duct 41a of the compactor 37a extends along the entire length of the compactor in this embodiment. The chute 38a which delivers shredded wastes from the shredder 33a to the open topped compactor compartment 44a in this case slopes towards front wall 27a as well as towards first end 14a of the housing 12a and delivers the shredded wastes to compartment 44a through an opening 97 in the front wall.

An advantage of the waste processor 11a is that the compactor now forms an elevated platform 98 on which persons can stand while depositing waste material in the sterilizer 18a through entry door 23a. An inclined ramp 99 can be provided to enable such persons to walk onto the platform 98 and to roll a cart onto the platform if that is desired. The arrangement also facilitates direct entry of non-infectious wastes into the compactor compartment 44a as such wastes may simply be dropped into the compartment. Persons standing on platform 98 may be protected by a wall 101 that extends upward from the edge of the platform that is spaced outward from housing front wall 27a and which is angled to connect with the first end 14a of the housing. A cross rail 102 extends between wall 101 and housing front wall 27a at the end of platform 98 that is adjacent the open top region of compactor duct 41a to limit movement of persons to the platform region of the compactor 37a.

The waste processor 11a may otherwise be similar to the first embodiment of the invention as described with reference to FIGS. 1 to 7.

Figure 12:
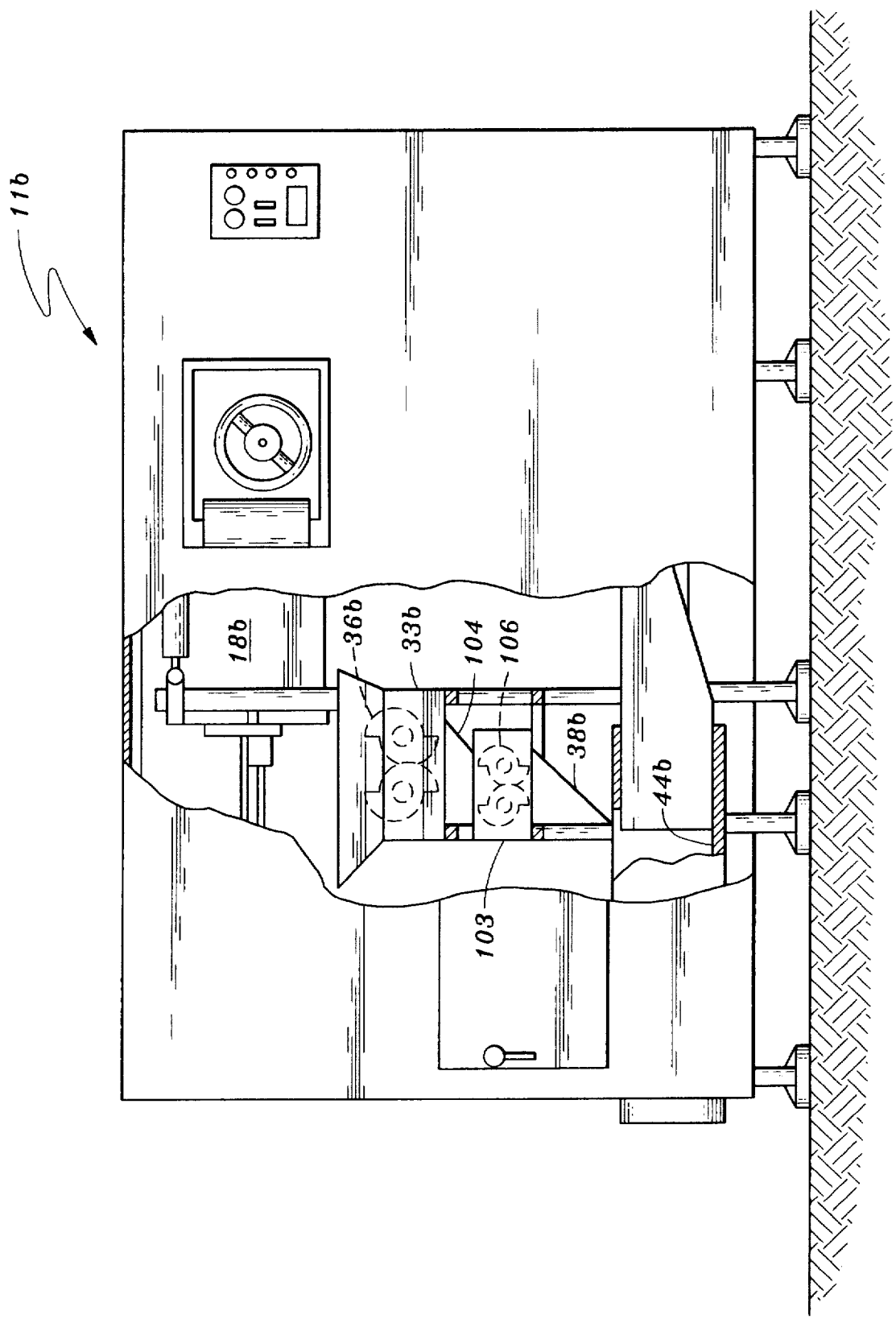
FIG. 12 is a broken out front elevation view of another infectious waste processor in accordance with a third embodiment of the invention.

Referring to FIG. 12, the shredding operation can be performed more efficiently if it is performed in stages. For this purpose, a second shredder 103 may be disposed below the first shredder 33b that receives the outflow of wastes from the sterilizer 18b. The second shredder 103 has an intake hopper 104 positioned to receive the outflow of shredded wastes from the first shredder 33b and an inclined chute 38b delivers the outflow from the second shredder to compactor compartment 44b.

The first shredder 33b has relatively large rotary cutting blades 36b sized to fragmentize large hard objects which may be present in the waste such as metal prostheses for example. The second shredder 103 has smaller cutting blades 106 sized to reduce the fragments produced by the first shredder 33b to still smaller fragments. The second shredder 103 may also be of smaller overall size as the bulk of the flow of wastes is substantially reduced by the shredding which occurs in the first shredder 33b The waste flow can be passed through additional shredders having progressively smaller cutting means if desired.

The shredders 33b and 103 can be replaced with other types of fragmentizing apparatus, such as grinding apparatus for example, that reduces material to progressively smaller fragments in a staged manner.

The waste processor 11b of FIG. 12 is of greater height than the previously described embodiments in order to accommodate to the presence of the second shredder 103 but may otherwise be of similar construction except as has herein been described.

While the invention has been described with respect to certain specific embodiments for purposes of example, many modifications and variations of the apparatus and method are possible and it is not intended to limit the invention except as defined in the following claims.

I claim:

1. A bio-hazardous waste material processing installation having a sterilizer which includes a sterilizing chamber for receiving said waste material, waste material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, wherein said sterilizer has a waste discharge opening through which said waste material discharging means ejects waste material from said chamber and has an openable door at said discharge opening and wherein said compactor and said fragmentizer and said sterilizing chamber are at progressively greater elevations within said installation, said fragmentizer intake being below said discharge opening and said fragmentizer outlet being above said compactor, wherein said sterilized waste receiving compartment of said compactor has an open top which extends horizontally to a location at which said open top is unobstructed by said fragmentizer whereby waste material that does not require sterilizing may be directly deposited in said compartment through said open top of said compartment.

2. The apparatus of claim 1 wherein said waste discharge opening and openable door are at one end of said sterilizer and wherein said sterilizer has a front wall which extends substantially at right angles to said waste discharge opening and openable door, said front wall having a waste entry opening therein and a second openable door thereat and wherein said compactor extends underneath said fragmentizer and away therefrom to said location at which said open top is unobstructed by said fragmentizer, and wherein said front wall has another opening and openable door thereat located to provide direct access to said open top of said compactor compartment.

3. A bio-hazardous waste material processing installation having a sterilizer which includes a sterilizing chamber for receiving said waste material, waste material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, wherein said sterilizer is at an elevated location and has a front wall with a waste material entry opening therein and an openable door thereat and wherein said compactor extends in parallel relationship with said front wall of said sterilizer at a location which is offset from the region beneath said sterilizer and forms an elevated platform which extends at a level that is below the level of said openable door.

4. A bio-hazardous waste material processing installation having a sterilizer which includes a sterilizing chamber for receiving said waste material, waste material election means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, wherein said sterilizer has a waste material entry opening and a first door thereat and a waste material discharge opening with a second door thereat, said discharge opening and second door being at an elevation which is higher than the elevation of said fragmentizer intake, wherein said waste material discharging means travels said second door progressively further outward from said discharge opening during periods when material is being discharged from said chamber and wherein said discharging means includes a movable waste ejection member which is disposed in said sterilization chamber and which extends across said chamber in position to sweep sterilized waste material towards said discharge opening when said ejection member is traveled towards said discharge opening, said ejection member being coupled to said second door for travel therewith.

5. The apparatus of claim 4 further including means for traveling said ejection member towards said second door and away therefrom whereby ejection of waste material may be continued after motion of said second door has been stopped.

6. The apparatus of claim 5 wherein said means for traveling said ejection member towards said second door and away therefrom includes a threaded shaft attached to said second door and extending to said ejection member and having a threaded engagement therewith, and means for rotating said shaft.

7. A bio-hazardous waste material processing installation having a sterilizer which includes a sterilizing chamber for receiving said waste material, waste material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, wherein said sterilizer has a waste material entry opening and a first door thereat and a waste material discharge opening with a second door thereat, said discharge opening and second door being at an elevation which is higher than the elevation of said fragmentizer intake, wherein said waste material discharging means travels said second door progressively further outward from said discharge opening during periods when material is being discharged from said chamber and wherein said discharging means includes a movable waste election member which is disposed in said sterilization chamber and which extends across said chamber in position to sweep sterilized waste material towards said discharge opening when said ejection member is traveled towards said discharge opening, said ejection member being coupled to said second door for travel therewith, further including means for traveling said ejection member towards said second door and away therefrom whereby ejection of waste material may be continued after motion of said second door has been stopped and wherein said means for traveling said ejection member towards said second door and away therefrom includes a threaded shaft attached to said second door and extending to said election member and having a threaded engagement therewith, and means for rotating said shaft, further including a first pair of guide rails extending along the path of travel of said second door, said second door having members which engage said first rails to support said second door during travel thereof, a second pair of guide rails secured to said second door and extending within said sterilizing chamber to said ejection member, said ejection member having members which engage said second pair of guide rails to support said ejection member.

8. The apparatus of claim 4 wherein said sterilizing chamber has first and second opposite ends and a front wall extending therebetween, said entry opening and first door being at said front wall and said discharge opening and second door being at said second end of said chamber and wherein said ejection member is spaced from said second door by a distance which situates said ejection member at said first end of said chamber when said second door is seated at said second end of said chamber.

9. The apparatus of claim 4 wherein said ejection member has a surface which faces said second door and wherein at least the lower region of said surface slopes downward in the direction of said second door.

10. A bio-hazardous waste material processing installation having a sterilizer which includes a sterilizing chamber for receiving said waste material, waster material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, further including a second waste material fragmentizer positioned to receive said flow of fragmentized sterilized waste material from said one fragmentizer prior to delivery of said flow of fragmentized waste material to said compactor compartment.

11. The apparatus of claim 10 wherein said one fragmentizer has first fragmenting means for reducing material to pieces of a first maximum size and said second fragmentizer has second fragmenting means for reducing said pieces of a first maximum size to pieces of a smaller maximum size.

12. The apparatus of claim 11 wherein said fragmentizers are shredders, said one fragmentizer having cutting blades of a first size and said second fragmentizer having cutting blades of a smaller size.

13. A bio-hazardous waste material processing installation having a sterilizer which includes a sterilizing chamber for receiving said waste material, waste material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, wherein said sterilizing chamber is at a location which is above and vertically spaced apart from the location of said compactor compartment and has a waste discharge opening through which said waste discharging means ejects said sterilized waste material from said chamber and wherein said intake of said one waste material fragmentizer is situated below said discharge opening in position to receive material which is discharged from said chamber, further including a second waste material fragmentizer having a second intake which is situated below said outlet of said one fragmentizer in position to receive fragmentized material which is released therefrom, said one fragmentizer having first fragmenting means for producing pieces of material that have a first maximum size and said second fragmentizer having second fragmenting means for producing pieces of material that have a second smaller maximum size.

14. A bio-hazardous waste material processing installation having a sterilizer which includes a sterilizing chamber receiving said waste material, waste material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump or the like, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, wherein said sterilizing chamber has an end with a sealable waste material discharge opening thereat and wherein said compactor compartment has an open end through which said compactor discharges waste material and wherein said compactor compartment and said fragmentizer and said sterilizing chamber are at progressively higher elevations and said fragmentizer and said end of said sterilizing chamber are progressively more distant from said open end of said compactor compartment, further including means for guiding material which drops from sterilizing chamber discharge opening to said fragmentizer intake and means for guiding material which drops from said fragmentizer to said compactor compartment.

15. A bio-hazardous waste material processing installation having a sterilizer which includes a sterilizing chamber for receiving said waste material, waste material election means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartment, further including a feed ram for forcing said sterilized waste material into said fragmentizer intake and motor means for traveling said ram towards said fragmentizer intake and away therefrom, further including a pivotable arm having a first end that is movable towards said fragmentizer intake and away therefrom along a curved path and wherein said feed ram is pivoted to said first end of said arm, wherein said motor means include a first motor coupled to said arm to pivot said first end thereof along said curved path and a second motor coupled to said feed ram to pivot said ram relative to said first arm whereby said feed ram may be maintained in parallel relationship with said fragmentizer intake as it approaches said intake along said curve path.

16. A bio-hazardous waste material processing installation having a sterilizer which includes a sterilizing chamber for receiving said waste material, waste material ejection means for discharging a flow of sterilized waste material from said sterilizing chamber and a compactor having a sterilized waste material receiving compartment and having means for forcing the contents thereof into an adjacent receptacle which is separable from said compactor and which may be transported to a dump, wherein the improvement comprises:

at least one waste material fragmentizer having an intake positioned to receive said flow of sterilized waste material as it is being discharged from said sterilizing chamber and having means for concurrently delivering a flow of fragmentized sterilized waste material to said compactor compartments.

further including a feed ram for forcing said sterilized waste material into said fragmentizer intake and motor means for traveling said ram towards said fragmentizer intake and away therefrom, wherein said sterilizer has a sterilized waste material discharge opening and a door thereat which is retractable from said opening along a path of travel and wherein said motor means enables retraction of said feed ram from said path of travel of said door.

17. Apparatus for processing bio-hazardous waste material comprising:

an upwardly extending support framework having a lower region, an intermediate region and an upper region;

a waste compactor disposed at said lower region of said framework and being secured thereto and having a horizontally extending waste material compartment with an open end and means for forcing the contents of said compartment out of said open end;

a waste material sterilizer disposed at said upper region of said framework and being secured thereto and having a sealable sterilizing chamber for receiving said bio-hazardous waste material and means for injecting pressurized steam into said chamber to sterilize the contents thereof, said chamber having an end with a sterilized waste material discharge opening thereat, said end of said chamber being horizontally spaced apart from the location of said open end of said compactor compartment;

means for discharging sterilized waste material from said chamber through said discharge opening thereof; and a waste material fragmentizer disposed at said intermediate region of said framework and being secured thereto, said fragmentizer being horizontally spaced apart from the location of said open end of said compactor compartment by a distance that is smaller than the spacing of said end of said sterilization chamber therefrom, said fragmentizer having an intake located to receive waste material that is discharged from said sterilization chamber and having an outlet from which fragmented waste material is delivered to said compactor compartment.

18. The apparatus of claim 17 wherein said fragmentizer includes a plurality of waste material shredders secured to said framework further including means for passing sterilized waste material from said sterilizing chamber through each of said shredders prior to delivery of said material to said compactor compartment and wherein a first of said plurality of shredders has first cutting means for cutting said waste materials into pieces of a first maximum size and wherein a second of said shredders has second cutting means for cutting said material into pieces which have a smaller maximum size.

19. In a method of processing bio-hazardous waste materials, the steps comprising:

subjecting said waste materials to pressurized steam within a sealed chamber for a period sufficient to sterilize said waste materials, fragmentizing the sterilized waste material by directing an outflow of waste material from said chamber into a fragmentizer wherein said fragmentizer reduces said waste materials to pieces having a first maximum size, concurrently directing an outflow of fragmented waste material from said fragmentizer into a compactor, compacting said fragmented sterilized waste material into a transportable container, including the further step of further reducing said waste materials to pieces having a second smaller maximum size by directing said outflow of fragmented sterilized waste material from said fragmentizer through a second fragmentizer as said material is traveling to said compactor.

* * * * *

UNITED STATES PATENT AND TRADEMARK OFFICE
CERTIFICATE OF CORRECTION

PATENT NO.  : 5,614,157

DATED       : March 25, 1997

INVENTOR(S) : John L. Hall

It is certified that error appears in the above-identified patent and that said Letters Patent is hereby corrected as shown below:

On the Title Page [*] Notice should read;

The term of this patent shall not extend beyond the expiration date of Pat. No. 5,389,347.

Signed and Sealed this

Eighth Day of July, 1997

*Attest:*

BRUCE LEHMAN

*Attesting Officer*    *Commissioner of Patents and Trademarks*